United States Patent
Bianchi et al.

(10) Patent No.: US 7,262,175 B2
(45) Date of Patent: Aug. 28, 2007

(54) SYNTHETIC OLIGONUCLEOTIDES AS INDUCERS OF ERYTHROID DIFFERENTIATION

(75) Inventors: Nicoletta Bianchi, Mezzogoro (IT); Giordana Feriotto, Occhiobello (IT); Roberto Gambari, Bologna (IT); Carlo Mischiati, Occhiobello (IT)

(73) Assignees: Universita' Degli Studi Di Ferrara, Ferrara (IT); Associazione Veneta Per La Lotta Alla Talassemia, Ferrara (IT); Associazione Per La Lotta Alla Talassemia Di Ferrara, Ferrara (IT); Chiesi Farmaceutici S.p.A., Parma (IT)

( * ) Notice: Subject to any disclaimer, the term of this patent is extended or adjusted under 35 U.S.C. 154(b) by 187 days.

(21) Appl. No.: 10/220,310

(22) PCT Filed: Mar. 13, 2001

(86) PCT No.: PCT/EP01/02804

§ 371 (c)(1),
(2), (4) Date: Sep. 13, 2002

(87) PCT Pub. No.: WO01/68147

PCT Pub. Date: Sep. 20, 2001

(65) Prior Publication Data

US 2003/0073660 A1 Apr. 17, 2003

(30) Foreign Application Priority Data

Mar. 13, 2000 (IT) .......................... TO2000A0234

(51) Int. Cl.
*A61K 31/70* (2006.01)
*C07H 21/04* (2006.01)
*C07H 21/02* (2006.01)
*C12Q 1/68* (2006.01)

(52) U.S. Cl. ...................... 514/44; 536/23.1; 536/24.1; 536/24.5; 435/6; 435/375; 435/377

(58) Field of Classification Search ................ 536/24.5
See application file for complete search history.

(56) References Cited

U.S. PATENT DOCUMENTS 5,763,488 A 6/1998 Bemis et al.
6,022,738 A * 2/2000 Atweh ...................... 435/320.1

FOREIGN PATENT DOCUMENTS

WO WO96/40271 12/1996
WO WO9712042 A2 * 4/1997

OTHER PUBLICATIONS

Agrawal et al. Antisense therapeutics: is it as simple as complementary base recognition? 2000 Mol. Med. Today: Reviews. vol. 61, pp. 72-81.*

Opalinska et al. Nucleic acid therapeutics: basic principlese and recent applications. 2002 Nature Reviews: Drug Discovery vol. 1, pp. 503-514.*

Jen et al. Suppression of gene expression by targeted disruption of messenger RNA: available options and current strategies 2000 Stem Cells vol. 18, pp. 307-319.*

Crooke, S. Progress in antisense technology 2004 Annu. Rev. Med. vol. 55, pp. 61-95.*

Madalyn Castle et al.; Blood, vol. 82, No. 4, pp. 1344-1350, Aug. 15, 1993. See PCT search report.

Wendy Magis et al.; Biochem. Biophys. Res. Commun.; vol. 214, No. 3, pp. 927-933, Sep. 25, 1995. See PCT search report.

G. Joan Grindlay et al.; Nucleic Acids Research; vol. 12, No. 4, pp. 1811-1820, 1984. See PCT search report.

Scott D. Langdon et al.; Blood, vol. 91, No. 1, pp. 309-318, Jan. 1, 1998. See PCT search report.

J. DeSimone et al.; Proc. Natl. Acad. Sci. USA, vol. 79, pp. 4428-4431, Jul. 1982, "5-Azacytidine Stimulates Fetal Hemoglobin Synthesis in Anemic Baboons".

C. H. Lowrey, et al.; The New England Journal of Medicine, vol. 329; pp. 845-848, Sep. 16, 1993, No. 12 Next; "Treatment With Azacitidine of Patients With End-Stage β-Thalassemia".

S. P. Perrine et al.: The New England Journal of Medicine, vol. 328; pp. 81-86; Jan. 14, 1993; A Short-Term Trial of Butyrate to Stimulate Fetal-Globin-Gene Expression in the β-Globin Disorders.

G.P. Rodgers et al.: The New England Journal of Medicine; vol. 328, pp. 73-80; Jan. 14, 1993, No. 2 Next; "Augmentation by Erythropoietin of the Fetal-Hemoglobin Response to Hydroxyurea in Sickle Cell Disease".

Rodgers et al—British Journal of Haematology vol. 91, pp. 263-268, (1995); "Novel Treatment Options in the Severe β-Globin Disorders".

S. Torkelson, et al.: Blood Cells, Molecules, and Disease (1996) 22(14) Jul. 31: pp. 150-158; "Erythroid Progenitor Proliferation is Stimulated by Phenoxyacetic and Phenylalkyl Acids".

J. Rochette et al.: Blood Reviews (1994) vol. 8; pp. 213-224; "Fetal Hemoglobin Levels in Adults".

O. Nakajima et al.: Federation of European Biochemical Societies, Sep. 1993), vol. 330, No. 1, pp. 81-84: "Enhancement by Retinoid of Hemin-Induced Differentiation of Human Leukemia K562 Cell Line".

N. Bianchi et al.: British Journal of Haematology, (1999), vol. 104; pp. 258-265: "The DNA-binding Drugs Mithramycin and Chromomycin are Powerful Inducers of Erythroid Differentiation of Human K562 Cells".

(Continued)

*Primary Examiner*—Sean McGarry
(74) *Attorney, Agent, or Firm*—Westerman, Hattori, Daniels & Adrian, LLP.

(57) ABSTRACT

The invention refers to a synthetic double-stranded oligonucleotide having a length comprised between 10 and 50 bases and a nucleic acid sequence selected from the group consisting of: (a) sequences corresponding to a selected portion of the promoter of human γ-globin gene; and (b) sequences corresponding to a selected portion of the human genomic region comprised between the γ-globin gene and the δβ-cluster, for use as an inducer of erythroid differentiation.

9 Claims, No Drawings

OTHER PUBLICATIONS

S. Castaigne, et al.: Blood, vol. 76, No. 9, Nov. 1, 1990: pp. 1704-1709: "All-Trans Retinoic Acid as Differentiation Therapy for Acute Promyelocytic Leukemia. I. Clinical Results". The New England Journal of Medicine, vol. 327, No. 8, Aug. 20, 1992, pp. 569-570.

T. Ikuta et al.: Annals of New York Academy of Sciences; pp. 87-99: "Cellular and Molecular Effects of a Pulse Butyrate Regimen and New Inducers of Globin Gene Expression and Hematopoiesis".

C. B. Lozzio et al.: Blood, vol. 45, No. 3 (Mar.), 1975; pp. 321-334: "Human Chronic Myelogenous Leukemia Cell-Line With Positive Philadelphia Chromosome".

R. Gambari, et al.: Experientia 41 (1985), pp. 673 & 675; Birkhäuser Verlag, CH-4010 Basel/Switzerland; "Efficient Cell Proliferation and Predominant Accumulation of ε-globin mRNA in human Leukemic K562 Cells Which Produce Mostly Hb Gower 1".

R. Gambari, et al.: Cell Differentiation, 14 (1984) pp. 87-97; Elsevier Scientific Publishers Ireland, Ltd.; pp. 87-97: "Human Leukemia K-562 Cells: Induction of Erythroid Differentiation by 5-azacytidine".

Rutherford R.E. Gale et al.: Nature, vol. 280, Jul. 12, 1979, pp. 164-165: "K562 Human Leukaemic Cells Synthesise Embryonic Haemoglobin in Response to Haemin".

Sambrook et al. Molecular Cloning—2nd edition Extraction, Purification, and Analysis of Messenger RNA from Eukaryotic Cells, 7.43-7.45: "Electrophoresis of RNA through Gels Containing Formaldehyde".

R. Cortesi et al.: European Journal of Haematology (1998), 61, pp. 295-301: "Human Leukemic K562 Cells Treated With Cytosine Arabinoside: Enhancement of Erythroid Differentiation by Retinoic Acid and Retinol".

Holland et al.: Proc. Natl. Acad. Sci., USA, vol. 88, pp. 7276-7280, Aug. 1991, Biochemistry: "Detection of Specific Polymerase Chain Reaction Product by Utilizing the 5'→3' Exonuclease Activity of *Thermus aquaticus* DNA polymerase".

Al-Khatti et al.: Concise Report, Blood, vol. 72, No. 2 (Aug. 1988); pp. 817-819: "Cooperative Enhancement of F-Cell Formation in Baboons Treated With Erythropoietin and Hydroxyurea".

Wolfgang Pfleiderer, et al.: Nucleic Acids Research, Symposium Series No. 7, 1980; pp. 61-71.

* cited by examiner

SEQUENCE LISTING

<160> NUMBER OF SEQ ID NOS: 9

<210> SEQ ID NO 1
<211> LENGTH: 331
<212> TYPE: DNA
<213> ORGANISM: Homo sapiens

<400> SEQUENCE: 1

| | | | | | |
|---|---|---|---|---|---|
| aagtcctggt | atcttctatg | gtgggagaag | aaaactagct | aaagggaaga | ataaattaga | 60 |
| gaaaaattgg | aatgactgaa | tcggaacaag | gcaaaggcta | taaaaaaaat | taagcagcag | 120 |
| tatcctcttg | ggggcccctt | ccccacacta | tctcaatgca | aatatctgtc | tgaaacggtt | 180 |
| cctggctaaa | ctccacccat | gggttggcca | gccttgcctt | gaccaatagc | cttgacaagg | 240 |
| caaacttgac | caatagtctt | agagtatcca | gtgaggccag | gggccggcgg | ctggctaggg | 300 |
| atgaagaata | aaaggaagca | cccttcagca | g | | | 331 |

<210> SEQ ID NO 2
<211> LENGTH: 13700
<212> TYPE: DNA
<213> ORGANISM: Homo sapiens

<400> SEQUENCE: 2

| | | | | | |
|---|---|---|---|---|---|
| ctcttgccca | tgattcagag | ctttcaagga | taggctttat | tctgcaagca | atacaaataa | 60 |
| taaatctatt | ctgctgagag | atcacacatg | attttcttca | gctctttttt | ttacatcttt | 120 |
| ttaaatatat | gagccacaaa | gggtttatat | tgagggaagt | gtgtatgtgt | atttctgcat | 180 |
| gcctgtttgt | gtttgtggtg | tgtgcatgct | cctcatttat | ttttatatga | gatgtgcatt | 240 |
| ttgatgagca | aataaaagca | gtaaagacac | ttgtacacgg | gagttctgca | agtgggagta | 300 |
| aatggtgttg | gagaaatccg | gtgggaagaa | agacctctat | aggacaggac | ttctcagaaa | 360 |
| cagatgtttt | ggaagagatg | ggaaaaggtt | cagtgaagac | ctgggggctg | gattgattgc | 420 |
| agctgagtag | caaggatggt | tcttaatgaa | gggaaagtgt | tccaagcttt | aggaattcaa | 480 |
| ggtttagtca | ggtgtagcaa | ttctatttta | ttaggaggaa | tactatttct | aatggcactt | 540 |
| agcttttcac | agcccttgtg | gatgcctaag | aaagtgaaat | taatcccatg | ccctcaagtg | 600 |
| tgcagattgg | tcacagcatt | tcaagggaga | gacctcattg | taagactctg | ggggaggtgg | 660 |
| ggacttaggt | gtaagaaatg | aatcagcaga | ggctcacaag | tcagcatgag | catgttatgt | 720 |
| ctgagaaaca | gaccagcact | gtgagatcaa | aatgtagtgg | gaagaatttg | tacaacatta | 780 |
| attggaaggt | ttacttaatg | gaattttgt | atagttggat | gttagtgcat | ctctataagt | 840 |
| aagagtttaa | tatgatggtg | ttacggacct | ggtgtttgtg | tctcctcaaa | attcacatgc | 900 |
| tgaatcccca | actcccaact | gaccttatct | gtggggagg | cttttgaaaa | gtaattaggt | 960 |
| ttagctgagc | tcataagagc | agatccccat | cataaaatta | ttttccttat | cagaagcaga | 1020 |
| gagacaagcc | atttctcttt | cctcccggtg | aggacacagt | gagaagtccg | ccatctgcaa | 1080 |
| tccaggaaga | gaaccctgac | cacgagtcag | ccttcagaaa | tgtgagaaaa | aactctgttg | 1140 |
| ttgaagccac | ccagtctttt | gtattttgtt | atagcacctt | acactgagta | aggcagatga | 1200 |
| agaaggagaa | aaaataagc | ttgggttttg | agtgaactac | agaccatgtt | atctcaggtt | 1260 |
| tgcaaagctc | ccctcgtccc | ctatgtttca | gcataaaata | cctactctac | tactctcatc | 1320 |
| tataagaccc | aaataataag | cctgcgccct | tctctctaac | tttgatttct | cctatttta | 1380 |
| cttcaacatg | ctttactcta | gccttgtaat | gtctttacat | acagtgaaat | gtaaagttct | 1440 |

-continued

```
ttattcttt   tttctttctt   tcttttttct   cctcagcctc   agaatttggc   acatgccctt   1500
ccttctttca   ggaacttctc   caacatctct   gcctggctcc   atcatatcat   aaaggtccca   1560
cttcaaatgc   agtcactacc   gtttcaggat   atgcactttc   tttcttttt   gttttttgtt   1620
ttttttaagt   caaagcaaat   ttcttgagag   agtaaagaaa   taaacgaatg   actactgcat   1680
aggcagagca   gccccgaggg   ccgctggttg   ttccttttat   ggttatttct   tgatgatatg   1740
ttaaacaagt   tttggattat   ttatgccttc   tctttttagg   ccatataggg   taactttctg   1800
acattgccat   ggcatgtttc   ttttaattta   atttactgtt   accttaaatt   caggggtaca   1860
cgtacaggat   atgcaggttt   gttttatagg   taaaagtgtg   ccatggtttt   aatgggtttt   1920
ttttttcttg   taaagttgtt   taagtttctt   gtttactctg   gatattggcc   tttgtcagaa   1980
gaatagattg   gaaaatcttt   ttcccattct   gtagattgtc   tttcgctctg   atggtagttt   2040
cttttgctga   gcaggagctc   tttagtttaa   ttagattcca   ttggtcaatt   tttgcttttg   2100
ctgcaattgc   ttttcacgct   ttcatcatga   aatctgtgcc   cgtgtttata   tcatgaatag   2160
tattgccttg   attttttttct   aggcttttta   tagtttgggg   ttttttcattt   aagtctctaa   2220
tccatccgga   gttaattttg   gataaggtat   aaggaaggag   tccagtttca   tttttcagca   2280
tatggctagc   cagttctccc   ccatcattta   ttaaattgaa   aatcctttcc   ccattgcttg   2340
cttttgtcag   gttctaaaa   gacagatggt   tgtaggtaca   atatgcagtt   tcttcaagtc   2400
atataatacc   atctgaaatc   tcttattaat   tcatttcttt   tagtatgtat   gctggtctcc   2460
tctgctcact   atagtgaggg   caccattagc   cagagaatct   gtctgtctag   ttcatgtaag   2520
attctcagaa   ttaagaaaaa   tggatggcat   atgaatgaaa   cttcatggat   gacatatgga   2580
atctaatgtg   tatttgttga   attaatgcat   aagatgcaac   aagggaaagg   ttgacaactg   2640
cagtgataac   ctggtattga   tgatataaga   gtctatagat   cacagtagaa   gcaataatca   2700
tggaaaacaa   ttggaaatgg   ggaacagcca   caaacaagaa   agaatcaata   ctaccaggaa   2760
agtgactgca   ggtcactttt   cctggagcgg   gtgagagaaa   agtggaagtt   gcagtaactg   2820
ccgaattcct   ggttggctga   tggaaagatg   gggcaactgt   tcactggtac   gcagggtttt   2880
agatgtatgt   acctaaggat   atgaggtatg   gcaatgaaca   gaaattcttt   tgggaatgag   2940
ttttagggcc   attaaaggac   atgacctgaa   gtttcctctg   aggccagtcc   ccacaactca   3000
atataaatgt   gtttcctgca   tatagtcaaa   gttgccactt   cttttttcttc   atatcatcga   3060
tctctgctct   taaagataat   cttggttttg   cctcaaactg   tttgtcacta   caaacttcc   3120
ccatgttcct   aagtaaaaca   ggtaactgcc   tctcaactat   atcaagtaga   ctaaaatatt   3180
gtgtctctaa   tatcagaaat   tcagctttaa   tatattgggt   ttaactcttt   gaaatttaga   3240
gtctccttga   aatacacatg   ggggtgattt   cctaaacttt   atttcttgta   aggatttatc   3300
tcagggtaa   cacacaaacc   agcatcctga   acctctaagt   atgaggacag   taagccttaa   3360
gaatataaaa   taaactgttc   ttctctctgc   cggtggaagt   gtgccctgtc   tattcctgaa   3420
attgcttgtt   tgagacgcat   gagacgtgca   gcacatgaga   cacgtgcagc   agcctgtgga   3480
atattgtcag   tgaagaatgt   ctttgcctga   ttagatataa   agacaagtta   aacacagcat   3540
tagactatag   atcaagcctg   tgccagacac   aaatgaccta   atgcccagca   cgggccacgg   3600
aatctcctat   cctcttgctt   gaacagagca   gcacacttct   cccccaacac   tattagatgt   3660
tctggcataa   ttttgtagat   atgtaggatt   tgacatggac   tattgttcaa   tgattcagag   3720
gaaatctcct   ttgttcagat   aagtacactg   actactaaat   ggattaaaaa   acacagtaat   3780
```

-continued

```
aaaacccagt ttttcccctta cttccctagt ttgtttctta ttctgctttc ttccaagttg    3840
atgctggata gaggtgttta tttctattct aaaaagtgat gaaattggcc gggcgcggtg    3900
gctcacacct gtaatcccag cactttggga ggctgaggtg ggcggatcac gaggtcagga    3960
gatcaagacc atcctggcta acatggtgaa accccatctc tactaaaaat acaaaaaatt    4020
agccagagac ggtggcgggt gcctgtagtc ccagctactc gggaggctga ggcaggagaa    4080
tggcgtgaac ctggaggca gagctgcagt gagcagagat cgcgccactg cacactccag    4140
cctgggtgac aaagcgagac tccatctcaa aaaaaaaaa aaaaaaaaa agaaagaaag    4200 aaagaaaaaa aaagtgatga aattgtgtat tcaatgtagt ctcaagagaa ttgaaaacca    4260
agaaaggctg tggcttcttc cacataaagc ctggatgaat aacaggataa cacgttgtta    4320
cattgtcaca actcctgatc caggaattga tggctaagat attcgtaatt cttatccttt    4380
tcagttgtaa cttattccta tttgtcagca ttcaggttat tagcggctgc tggcgaagtc    4440
cttgagaaat aaactgcaca ctggatggtg ggggtagtgt aggaaaatgg aggggaagga    4500
agtaaagttt caaattaagc ctgaacagca agttcccct gagaaggcca cctggattct    4560
atcagaaact cgaatgtcca tcttgcaaaa cttccttgcc caaaccccac ccctggagtc    4620
acaacccacc cttgaccaat agattcattt cactgaggga ggcaagggc tggtcaatag    4680 attcatttca ctgggagagg caaagggctg ggggccagag aggagaagta aaagccaca    4740 catgaagcag caatgcaggc atgcttctgg ctcatctgtg atcaccagga actcccaga    4800 tctgacactg tagtgcattt cactgctgac aagaaggctg ctgccaccag cctgtgaagc    4860
aaggttaagg tgagaaggct ggaggtgaga ttctgggcag gtaggtactg gaagccggga    4920
caaggtgcag aaaggcagaa agtgtttctg aaagagggat tagcccgttg tcttacatag    4980
tctgactttg cacctgctct gtgattatga ctatcccaca gtctcctggt tgtctaccca    5040
tggacctaga ggtactttga agttttggat tatctgggct ctgactgtgc aataatgggc    5100
aaccccaaag tcaaggcaca tggcaagaag gtgctgatct ccttcggaaa agctgttatg    5160
ctcacggatg acctcaaagg cacctttgct acactgagtg acctgcactg taacaagctg    5220
cacgtggacc ctgagaactt cctggtgagt agtaagtaca ctcacgcttt cttctttacc    5280
cttagatatt tgcactatgg gtacttttga aagcagaggt ggctttctct tgtgttatga    5340
gtcagctatg ggatatgata tttcagcagt gggattttga gagttatgtt gctgtaaata    5400
acataactaa aatttggtag agcaaggact atgaataatg gaaggccact taccatttga    5460
tagctctgaa aaacacatct tataaaaaat tctggccaaa atcaaactga gtgttttgga    5520
tgagggaaca gaagttgaga tagagaaaat aacatctttc ctttggtcag cgaaattttc    5580
tataaaaatt aatagtcact tttctgcata gtcctggagg ttagaaaaag atcaactgaa    5640
caaagtagtg ggaagctgtt aaagaggat tgtttccctc cgaatgatga tggtatactt    5700
ttgtacgcat ggtacaggat tctttgttat gagtgtttgg gaaaattgta tgtatgtatg    5760
tatgtatgtg atgactgggg acttatccta tccattactg ttccttgaag tactattatc    5820
ctacttttta aaaggacgaa gtctctaaaa aaaaatgaa acaatcacaa tatgttgggg    5880
tagtgagttg gcatagcaag taagagaagg ataggacaca atgggaggtg cagggctgcc    5940
agtcatattg aagctgatat ctagcccata atggtgagag ttgctcaaac tctggtcaaa    6000
aaggatgtaa gtgttatatc tatttactgc aagtccagct tgaggccttc tattcactat    6060
gtaccatttt cttttttatc ttcactccct ccccagctct taggcaacgt gatattgatt    6120
gttttggcaa cccacttcag cgaggatttt accctacaga tacaggcttc ttggcagtaa    6180
```

-continued

```
ctaacaaatg ctgtggttaa tgctgtagcc cacaagacca ctgagttccc tgtccactat    6240
gtttgtacct atgtcccaaa atctcatctc ctttagatgg gggaggttgg ggagaagagc    6300
agtatcctgc ctgctgattc agttcctgca tgataaaaat agaataaaga aatatgctct    6360
ctaagaaata tcattgtact cttttttctgt ctttatattt taccctgatt cagccaaaag   6420
gacgcactat ttctgatgga aatgagaatg ttggagaatg ggagtttaag gacagagaag    6480
atactttctt gcaatcctgc aagaaaagag agaactcgtg ggtggattta gtggggtagt    6540
tactcctagg aaggggaaat cgtctctaga ataagacaat gttttttacag aaagggaggt   6600 caatggaggt actctttgga ggtgtaagag gattgttggt agtgtgtaga ggtatgttag    6660
gactcaaatt agaagttctg tataggctat tatttgtatg aaactcagga tatagctcat    6720
ttggtgactg cagttcactt ctacttattt taaacaacat attttttatg atttataatg    6780
aagtggggat ggggcttcct agagaccaat caagggccaa accttgaact ttctcttaac    6840
gtcttcaatg gtattaatag agaattatct ctaaggcatg tgaactggct gtcttggttt    6900
tcatctgtac ttcatctgct acctctgtga cctgaaacat atttataatt ccattaagct    6960
gtgcatatga tagatttatc atatgtattt tccttaaagg attttttgtaa gaactaattg   7020 aattgatacc tgtaaagtct ttatcacact acccaataaa taataaatct ctttgttcag    7080
ctctctgttt ctataaatat gtacaagttt tattgttttt agtggtagtg attttattct    7140
ctttctatat atatacacac acatgtgtgc attcataaat atatacaatt tttatgaata    7200
aaaaattatt agcaatcaat attgaaaacc actgattttt gttatgtga gcaaacagca     7260 gattaaaagg ctgagattta ggaaacagca cgttaagtca agttgataga ggagaatatg    7320
gacatttaaa agaggcagga tgatataaaa ttagggaaac tggatgcaga gaccagatga    7380
agtaagaaaa atagctatcg ttttgagcaa aaatcactga agtttcttgc atatgagagt    7440
gacataataa atagggaaac gtagaaaatt gattcacatg tatatatata tatagaactg    7500
attagacaaa gtctaacttg ggtatagtca gaggagcttg ctgtaattat attgaggtga    7560
tggataaaga actgaagttg atggaaacaa tgaagttaag aaaaaaaatc gagtaagaga    7620
ccattgtggc agtgattgca cagaactgga aaacattgtg aaacagagag tcagagatga    7680
cagctaaaat ccctgtctgt gaatgaaaag aaggaaattt attgacagaa cagcaaatgc    7740
ctacaagccc cctgtttgga tctggcaatg aacgtagcca ttctgtggca atcacttcaa    7800
actcctgtac ccaagaccct taggaagtat gtagcaccct caaacctaaa acctcaaaga    7860
aagaggtttt agaagatata ataccctttc ttctccagtt tcattaatcc caaaacctct    7920
ttctcaaagt atttcctcta tgtgtccacc ccaaagagct cacctcacca tatctcttga    7980
gtgggagcac atagataggc ggtgctacca tctaacagct tctgaaattc ctttgtcata    8040
tttttgagtc cccactaata acccacaaag cagaataaat accagttgct catgtacaat    8100
aatcactcaa ctgctgtctt gtagcataca ttaattaagc acattctttg aataattact    8160
gtgtccaaac aatcacactt taaaatctca cacttgtgct atcccttgcc cttctgaatg    8220
tcactctgta tttttaaatga agagatgagg gttgaatttc ctgtgttact tattgttcat    8280
ttctcgatga ggagttttca cattcaccttt tactggaaaa cacataagta cacatcttac    8340
aggaaaaata taccaaactg acatgtagca tgaatgcttg tgcatgtagt catataaaat    8400
cttgtagcaa tgtaaacatt ctctgatata cacatacaga tgtgtctata tgtctacaca    8460
atttcttatg ctccatgaac aaacattcca tgcacacata agaacacaca ctgttacaga    8520
```

-continued

```
tgcatacttg agtgcattga caaaattacc ccagtcaatc tagagaattt ggatttctgc   8580
atttgactct gttagctttg tacatgctgt tcatttactc tgggtgatgt ctttccctca   8640
ttttgccttg tctatcttgt actcatactt taagtcctaa cttatatgtt atctcaacta   8700
agaagctatt ttttttttaat tttaactggg cttaaagccc tgtctataaa ctctgctaca   8760
attatgggct ctttcttata atatttagtg ttttttcctac taatgtactt aatctgctca   8820
ttgtatattc ctaccactaa attttaacct cttttatggt agagacattg tcttgtaaac   8880
tcttatttcc ctagtatttg gagatgaaaa aaaagattaa attatccaaa attagatctc   8940
tcttttctac attatgagta ttacactatc cataggggaag tttgtttgag acctaaactg   9000
aggaaccttt ggttctaaaa tgactatgtg atatcttagt atttataggt catgaggttc   9060
cttcctctgc ctctgctata gtttgattag tcagcaagca tgtgtcatgc atttattcac   9120
atcagaattt catacactaa taagacatag tatcagaagt cagttttatta gttatatcag   9180 ttagggtcca tcaaggaaag gacaaaccat tatcagttac tcaacctaga attaaataca   9240
gctcttaata gttaattatc cttgtattgg aagagctaaa atatcaaata aggacagtg    9300 cagaaatcta gatgttagta acatcagaaa acctcttccg ccattaggcc tagaagggca   9360
gaaggagaaa atgtttatac caccagagtc cagaaccaga gcccataacc agaggtccac   9420
tggattcagt gagctagtgg gtgctccttg gagagagcca gaactgtcta atgggggcat   9480
caaagtatca gccataaaaa accataaaaa agactgtctg ctgtaggaga tccgttcaga   9540
gagagagaga gaccagaaat aatcttgctt atgctttccc tcagccagtg tttaccattg   9600
cagaatgtac atgcgactga aagggtgagg aaacctggga aatgtcagtt cctcaaatac   9660
agaacacact gagggaagga tgagaaataa atgtgaaagc agacatgaat ggtaattgac   9720
agaaggaaac taggatgtgt ccagtaaatg aataattaca gtgtgcagtg attattgcaa   9780
tgattaatgt attgataaga taatatgaaa acacagaatt caaacagcag tgaactgaga   9840
ttagaattgt ggagagcact ggcatttaag aatgtcacac ttagaatgtg tctctaggca   9900
ttgttctgtg catatatcat ctcaatattc attatctgaa aattatgaat taggtacaaa   9960
gctcaaataa tttattttt caggttagca agaactttt tttttttttt tctgagatg    10020 gagcattgct atggttgccc aggctggagt gcaatggcat gatccaggct cactgcaaca  10080
tctgcctccc aggttcaagc gattctcctg cctcagcctc ccaagtagct ggcattacag  10140
gcatgtgcca ccaccatgcc tggctaattt tctatttta gtagataggg ggtttcacca   10200
tgttggtcag gctgatctcg aactcctaac atcaggtgat ccaccctcct cggcctctga  10260
atgtactggg atcacaggcg tgagccacca cacccagcca agaatgtgaa ttttgtagaa  10320
ggatataacc catatttctc tgaccctaga gtccttagta tacctcccat accatgtggc  10380
tcatcctcct tacatacatt tcccatcttt cacctacct tttccttttt gtttcagctt   10440
ttcactgtgt gtcaaaatct agaaccttat ctcctacctg ctctgaaacc aacagcaagt  10500
tgacttccat tctaacccac attggcatta cactaattaa aatcgatact gagttctaaa  10560
atcatctggg attttgggga ctatgtctta cttcatactt ccttgagatt tcacattaaa  10620
tgttggtgtt cattaaaggt ccttcattta actttgtatt catcacactc ttggattcac  10680
agttatatct aaactcttat atatagcctg tataatccca attcccaagt ctgatttcta  10740
acctctgacc tccaacctca gtgccaaacc catatatcaa acaatgtact gggcttattt  10800
atatagatgt cctataggca cctcagactc agcatggtaa tttcacttgt tatactaaaa  10860
ctgtttctct tccagtgttt tccatttag tcattagata gctacttgcc cattcaccaa   10920
```

```
ggtcacagat taaaatcatt tccctacctc taatcaacag ttcaattctg cttcaatttg      10980
tccctatcta ttaatcacca ctcttactgc ccagtcaggt cctcattgtt tcctgaacaa      11040
gagtagatgc tattctttcc actttaagac cttatcctgg ctggatgcgg tggctcaggc      11100
ttgtaaaccc agcactttgg gaggccgagg caggcagatc acttgaggtc aggagttcaa      11160
gaccagcctg accaacatgg tgaaacccca tctctactaa aaatacaaaa tcagccgggc      11220
gtgtggtgca tgcctgcagt cccagctatt caggtggctg aggcaggaga attgcttgaa      11280
cccaggaggc ggaggttgcg gtgagcctag attgcaccat tgcactctag cttgggcaat      11340
agggatgaaa ctccatctca gaagagaaaa gaaaaaaaga ccttattctg ttacacaaat      11400
cctctcaatg caatccatat agaataaaca tgtaaccaga tctcccaatg tgtaaaatca      11460
tttcaggtag aacagaatta aagtgaaaag ccaagtcttt ggaattaaca gacaaagttc      11520
aaataacagt cctcatggcc ttaagaattt acctaacatt ttttttagaa tcaattttct      11580
tatatatgaa ttggaaacat aattcctccc tcacaaacac attctaagat tttaaggaga      11640
tattgatgaa gtacatcatc tgtcattttt aacagttagt ggtagtgatt cacacagcac      11700
attatgatct gttcttgtat gttctgttcc attctgtatt cttgacctgg ttgtattctt      11760
tctgagctcc agatccacat atctaagtac atcttttttgc attttacaag agtgcataca      11820
atacaatgta tccaagactg tatttctgat tttatcgtac cactaaactc acaaatgtgg      11880
ccctattctt gtgttcacga ctgacatcac cgtcatggtc caagtctgat aatagaaatg      11940
gcattgtcac tttcttccct actgcaacag aagcccagct atttgtctcc cattttctct      12000
acttctaaaa tacatttctt cactaagtga gaataatctt ttaaagacac aaatcaaacc      12060
atgccaccac ctttcttgaa ttattcaata tctttcgttg gcttccaggt tacagaaaaa      12120
taacttgtaa caaagtttaa aggtcattca tggctcctct ctaccctatt ttataacatt      12180
tccccttgtg atcagaatct caggcacatc atccatcttt ctatatacaa ataaagtcat      12240
atagtttgaa ctcacctctg gttacttttta atcaaccaaa tgctgtaaaa tgcatttgta      12300
tcgctacgtg ttaagcagta gttgattctt ttcatttctt gttaatattc tattctttga      12360
ctataccgta atttatcaat tctactgttg gtaagcattt aagtggctac cggtttgagg      12420
tttttatgat tattgctgtc ataagcattt ctatacatgt ctttggatac acacatgcat      12480
gtgtttctga atatctaaaa atgtaattgc taggtaatag acttatcaag catccagcat      12540
ttgtggatac tattaaaggt tttccaaagg ggttatacta ttgtacagtg tcaccaacag      12600
agtttgagtt tctattgatc catatcacca ccaaaatttg aactgtcagt cttatctctt      12660
ctcttgtctc ttttttcctc ttttttttcc ttcccttccc ctctcttcgt ttcttttctc      12720
tcctcttctc ttctttcctc tcttcccttc cctttctctt tctcttccct atcccttctc      12780
ctctcctctc ccctccttttt ttcctcctctc ctctccatta tttatttttc cttcttctcc      12840
tccatccctt ccatcctctc tcttccctc ttccttcctt cctttctcca tttcttcctc      12900
ctctttccct caatccttcc ttttggatat gctcatgggt gtgtatttgt ctgccattgt      12960
ggcattattt gaattcagaa aagagtgaaa aactactggg atcttcattc tgggtctaat      13020
tccacatttt tttttaagaa cacactctgt aaaaatgttc tgtactagca tattcccagg      13080
aacttcgtta aatttaatct ggctgaatat ggtaaatcta ctttgcactt tgcattcttt      13140
ctttagtcat accataattt taaacattca aaatatttgt atataatatt tgattttatc      13200
tgtcattaaa atgttaacct taaaattcat gtttccagaa cctatttcaa taactggtaa      13260
```

```
ataaacacta ttcatttttt aaatattctt ttaatggata tttatttcaa tataataaaa    13320
aattagagtt ttattatagg aagaatttac caaaagaagg aggaagcaag caagtttaaa    13380
ctgcagcaat agttgtccat tccaacctct caaaattccc ttggagacaa aatctctaga    13440
ggcaaagaag aactttatat tgagtcaact tgttaaaaca tctgctttta gataagtttt    13500
cttagtataa agtgacagaa acaaataagt taaactctaa gatacattcc actatattag    13560
cctaaaacac ttctgcaaaa atgaaactag gaggatattt ttagaaacaa ctgctgaaag    13620
agatgcggtg gggagatatg cagaggagaa cagggtttct gagtcaagac acacatgaca    13680
gaacagccaa tctcagggca                                                13700

<210> SEQ ID NO 3
<211> LENGTH: 15
<212> TYPE: DNA
<213> ORGANISM: Homo sapiens

<400> SEQUENCE: 3
aaacggtccc tggct                                                        15

<210> SEQ ID NO 4
<211> LENGTH: 18
<212> TYPE: DNA
<213> ORGANISM: Homo sapiens

<400> SEQUENCE: 4
ctccacccat gggttggc                                                     18

<210> SEQ ID NO 5
<211> LENGTH: 19
<212> TYPE: DNA
<213> ORGANISM: Homo sapiens

<400> SEQUENCE: 5
atttctttct ttctttttt                                                    19

<210> SEQ ID NO 6
<211> LENGTH: 20
<212> TYPE: DNA
<213> ORGANISM: Homo sapiens

<400> SEQUENCE: 6
tgaatgaatg aacgaatgag                                                   20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:
      gamma-globin forward primer

<400> SEQUENCE: 7
tggcaagaag gtgctgactt c                                                 21

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:
      gamma-globin reverse primer

<400> SEQUENCE: 8
```

```
tcactcagct gggcaaagg                                                    19

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      gamma-globin probe

<400> SEQUENCE: 9
tgggagatgc cataaagcac ctgg                                              24
```

SYNTHETIC OLIGONUCLEOTIDES AS INDUCERS OF ERYTHROID DIFFERENTIATION

The present invention relates to the use of synthetic oligonucleotides which are capable of inducing erythroid differentiation for the manufacture of a medicament for the therapeutic treatment of β-thalassemia and neoplastic diseases, and to a pharmaceutical composition including at least one of the said oligonucleotides and a pharmaceutically acceptable carrier.

The existence of compounds which are able to induce the synthesis of fetal haemoglobin (HbF) in adults is known since long (1–7).

These compounds, herein referred to as "biological response modifiers", are able to activate the transcription of embryonic and fetal globin genes and to induce erythroid differentiation.

In human adults, the activation of the transcription of γ-globin genes leads to the production of HbF, which mimicks a HPFH (High Persistance of Fetal Hemoglobin) phenotype; this could reduce the severity of β-thalassemia in affected patients (8). Accordingly, recent studies have been focused on the search of compounds able to stimulate γ-globin gene expression at high levels, in an attempt to reduce transfusions in β-thalassemia patients (12, 13).

In addition, as it has been recently described (9, 10), a combined treatment with different biological response modifiers could lead to a further increase of the expression of γ-globin genes.

It is further known (11) that the treatment of neoplastic cells with compounds which are able to induce differentiation could be of interest in the therapy of some neoplastic diseases.

The object of the present invention is to find new biological response modifiers to be proposed for the treatment of β-thalassemia and/or neoplastic diseases, which exhibit low toxicity in vivo and a high level of induction of γ-globin gene expression.

Molecules which are able to induce differentiation, exhibiting only minor cytotoxic effects in vivo, could in fact reduce side effects when administered to patients in clinical trials.

The present inventors have unexpectedly found that double-stranded oligonucleotides having a nucleic acid sequence corresponding to portions of the β-like gene cluster, in particular to some sequences of the promoter of the human γ-globin gene and to some sequences comprised between the γ-globin gene and the δβ-gene region, show the said activity.

The present invention therefore provides a synthetic double-stranded oligonucleotide having a nucleic acid sequence selected from the group consisting of:
a) sequences corresponding to a selected portion of the promoter of human γ-globin gene; and
b) sequences corresponding to a selected portion of the human genomic region comprised between the γ-globin gene and the δβ-cluster, for use as an inducer of erythroid differentiation.

The nucleic acid sequence of the promoter of human γ-globin is SEQ. ID NO:1 and the nucleic acid sequence of the human genomic region comprised between the γ-globin gene and the δβ-cluster is SEQ. ID NO:2.

Advantageously, the double-stranded oligonucleotide of the invention has a length comprised between 10 and 50 bases, preferably between 10 and 30 bases, and a nucleic acid sequence corresponding to a selected portion of SEQ. ID NO:1 or SEQ. ID NO:2.

Preferably, the double-stranded oligonucleotide of the invention has a nucleic acid sequence selected within the portion of SEQ. ID NO:1 comprised between positions 220 and 290.

In the present description, the term "oligonucleotide" is meant to include also an oligonucleotide wherein the backbone has been modified according to the approaches commonly used for improving oligonucleotides' properties such as cellular uptake, target binding and/or stability. Such modifications include for example the modification of the linkage between the base and/or the sugar moieties. Among the current derivatives and/or techniques available for improving the oligonucleotides performances are the conjugation with lipophilic moieties, chimeric technology, peptide nucleic acids, aptamers.

As it will be further illustrated in the example, it has also been found that double-stranded oligonucleotides having a nucleic acid sequence as set forth in SEQ. ID NO:3, SEQ. ID NO:4 (corresponding to selected regions of the promoter of the human γ-globin gene), SEQ. ID NO:5 and SEQ. ID NO:6 (corresponding to selected regions comprised between the human γδβ-globin gene cluster are particularly suitable for inducing a high expression of γ-globin genes.

Therefore, the nucleic acid sequence of the double-stranded oligonucleotide of the invention is more preferably selected from the group consisting of SEQ. ID No:3, SEQ. ID NO: 4, SEQ. ID No:5 and SEQ. ID NO: 6.

The synthetic oligonucleotides of the invention are able to act by mimicking human γ-globin gene regulatory sequences and by potentially interacting with nuclear proteins, including transcription factors.

The person skilled in the art knows how to obtain a double stranded oligonucleotide; for example it may be obtained by synthesising a single-stranded oligonucleotide and then specifically annealing the single-stranded oligonucleotide with its complementary strand by forming Watson-Crick hydrogen bonds.

The annealing between the two complementary strands may be obtained for example by incubating the DNA in a solution of 150 mM NaCl at room temperature for about two hours. Methods for the synthesis of single-stranded oligonucleotides are found for example in (20).

In one embodiment of the invention, the synthetic double stranded oligonucleotide is used as an inducer of erythroid differentiation in combination with a second biological response modifier, preferably selected from the group consisting of cytosine arabinoside, retinoic acid, plicamycin, chromomycin, hydroxyurea, guanosine triphosphate (GTP), guanosine diphosphate (GDP), and guanosine monophosphate (GMP). Cytosine arabinoside and retinoic acid are more preferred.

Also within the scope of the invention is the use of a synthetic double stranded oligonucleotide as previously defined, eventually in combination with a second biological response modifier as previously defined, for the manufacture of a medicament for the treatment of β-thalassemia and/or neoplastic diseases.

The present invention also provides a pharmaceutical composition comprising at least a synthetic double stranded oligonucleotide as previously defined, eventually in combination with a second biological response modifier as previously defined, and a pharmaceutically acceptable carrier.

The activity of the double stranded synthetic oligonucleotides of the invention as inducers of erythroid differentiation has been assessed by determining the level of erythroid differentiation induced in a human cultured cell line, as reported in Table 1.

The following example is provided by way of illustration only and is not intended to limit in any way the scope of the invention.

EXAMPLE

The biological activity of the double stranded oligonucleotides represented by SEQ. ID NO: 3, SEQ. ID NO: 4, SEQ. ID NO: 5 and SEQ. ID NO: 6 has been evaluated by determining the ability of these oligonucleotides to induce erythroid differentiation of the human erythroleukemia K562 cell line, which is able to undergo erythroid differentiation and to increase γ-globin gene expression following treatment with a suitable biological response modifier (14–17). The level of erythroid differentiation has been evaluated by the benzidine-staining (16). The production of haemoglobin has been evaluated by cellulose acetate gel electrophoresis of cytoplasmic extracts and benzidine staining of the gels (16). The expression of γ-globin genes has been evaluated by RT-PCR (reverse transcriptase PCR) (18).

These assays have been performed after 6 days of induction with the above indicated double stranded oligonucleotides.

TABLE 1

| Oligonucleotide (SEQ. ID NOs) | Optimal Concentration (μg/ml) | *Erythroid differentiation (%) |
|---|---|---|
| 3 | 10 | 55 |
| 4 | 10 | 40 |
| 5 | 10 | 57 |
| 6 | 10 | 38 |

*Erythroid differentiation = proportion of benzidine-positive K562 cells.

In order to analyse hemoglobin production by erythroid induced K562 cells, 2 μl of total fresh post-mitochondrial cell lysates were electrophoresed on cellulose acetate strips in Tris-ethylenediamine-tetraacetic acid (EDTA)-borate buffer. After an electrophoresis of 30 min at 5 mA, the gels were stained with benzidine/hydrogen peroxide (1% benzidine in 4.3 M acetic acid, 3% $H_2O_2$) and photographed. The data obtained show that the Hb produced following erythroid induction is mainly Hb Portland. Quantitative real-time PCR assay (21) of γ-globin mRNA transcripts was carried out with the use of gene-specific double fluorescently labeled probes in a 7700 Sequence Detector (PE Biosystems, Warrington Cheshire, UK). The following primer and probe sequences were used for real-time PCR: γ-globin forward primer, 5'-TGG CAA GAA GGT GCT GAC TTC-3' (SEQ. ID NO:7); γ-globin reverse primer, 5'-TCA CTC AGC TGG GCA AAG G-3' (SEQ. ID. NO:8); γ-globin probe, 5'-FAM-TGG GAG ATG CCA TAA AGC ACC TGG-TAMRA-3' (SEQ. ID NO:9), where the fluorescent reporter FAM and the quencher TAMRA are 6-carboxy fluorescein (FAM) and 6-carboxy-N,N,N',N'-tetramethylrhodamine (TAMRA) respectively. The results obtained give evidence for an increase of γ-globin mRNA production. For instance, the oligonucleotide corresponding to SEQ. ID NO:3 induced a nine-fold increase of γ-globin mRNA production with respect to uninduced K562 cells.

The high level of biological activity and the expected low level of in vivo cytotoxicity of the oligonucleotides of the invention allow to propose these molecules as promising candidates for use in the development of pharmacological approaches for the treatment of β-thalassemia and/or neoplastic diseases.

REFERENCES

1. Al-Khatti A, Papayannopoulou T, Knitter G, Fritsch E F, Stamatoyannopoulos G, Blood, 72:817–819, 1988.
2. DeSimone J, Heller P, Hall L, Zwiers D, Proc. Natl. Acad. Sci. USA, 79:4428–4431, 1982.
3. Lowrey C H, Nienhuis A W, Engl. J. Med., 329:845–848, 1993.
4. Perrine S P, Ginder G D, Faller D V, et al., N. Engl. J. Med., 328:81–86, 1993.
5. Rodgers G P, Dover G J, Uyesaka N, Noguchi C T, Schechter A N, Nienhuis A W, N. Engl. J. Med., 328: 73–80, 1993.
6. Rodgers G P, Rachmilewitz E A, British J. Haematology, 91:263–268, 1995.
7. Torkelson S, White B, Faller D V, Phipps K, Pantazis C, Perrine S P, Blood Cells, Molecules and Diseases, 22:150–158, 1996.
8. Rochette J, Craig J E e Thein S L, Blood Reviews 8, 213-224, 1994.
9. Nakajima, O., Hashimoto, Y. e Iwasaki S., FEBS Letters, 330, 81–84, 1993.
10. Bianchi N, Osti F, Rutigliano C, Ginanni Corradini F, Borsetti E, Tomassetti M, Mischiati C, Feriotto G e Gambari R, British Journal of Haematology, 104:258–263, 1999.
11. Castaigne S, Chomienne C, Daniel M T, Ballerini P, Berger R, Fenaux P, Degos L., Blood, 76:1704, 1990.
12. Dover, G. J., Brusilow, S e Samid D, New England Journal of Medicine, 327: 569–570, 1992.
13. Ikuta, T., Atweh, G., Boosalis, V., White, G. L., De Fonseca, S., Boosalis, M., Faller, D. V., Perrine, S. P., Annals of New York Academy of Sciences, 850:87–99, 1998.
14. Lozzio C B, Lozzio B B., Blood, 45:321–334, 1975.
15. Gambari R, Amelotti F, Piva R., Experientia, 41:673–675, 1985.
16. Gambari R, del Senno L, Barbieri R, et al., Cell Differentiation, 14:87–97, 1984.
17. Rutherford T R, Clegg J B, Weatherall D J., Nature, 280:164–165, 1979.
18. Sambrook J, Fritsch, E F e Maniatis T, Extraction, purification and analysis of messenger RNA from eukaryotic cells. In: Molecular Cloning 2nd ed. Cold Spring Harbor, N.Y., Cold Spring Harbor Laboratory, 7.43–7.45, 1981.
19. Cortesi R, Gui V, Osti F, Nastruzzi C, Gambari R., Eur J Haematol, 61:295–301, 1998.
20. Pfleidrer W., Uhlmann E., Charubala R, Flockerzi D, Silber G, Varma R S. 1980. Recent progress in oligonucleotide synthesis. Nucleic Acids Symp. Ser., 7, 61–71.
21. Holland, P. M., Abramson, R. D., Watson, R. & Gelfand, D. H. 1991 Detection of specific polymerase chain reaction product by utilizing the 5' - - - 3 exonuclease activity of Thermus aquaticus DNA polymerase. Proceedings of National Academy of Sciences of the United States of America, 88 (16), 7276–7280.

The invention claimed is:

1. A synthetic double-stranded oligonucleotide of 15–50 bases
wherein the synthetic double-stranded oligonucleotide comprises the sequence of SEQ. ID NO. 3.

2. A pharmaceutical composition comprising at least the synthetic double-stranded oligonucleotide according to claim 1 and a pharmaceutically acceptable carrier.

3. A pharmaceutical composition comprising at least the synthetic double-stranded oligonucleotide according to claim 1, a further modifier of a biological response and a pharmaceutically acceptable carrier.

4. The pharmaceutical composition according to claim 3, wherein said further modifier of the biological response is plicamycin.

5. The synthetic double-stranded oligonucleotide according to claim 1, in combination with a further biological response modifier selected from the group consisting of cytosine arabinoside, retinoic acid, plicamycin, chromomycin, hydroxyurea, guanosine triphosphate (GTP), guanosine diphosphate (GDP), guanosine monophosphate (GMP).

6. A method of therapeutic treatment, comprising:

administering a synthetic double-stranded oligonucleotide of 15-50 bases to a patient,
wherein said synthetic double-stranded oligonucleotide comprises the sequence of SEQ. ID NO. 3.

7. The method of therapeutic treatment of claim 6, further comprising:

administering a pharmaceutically acceptable to carrier to the patient.

8. The method of therapeutic treatment of claim 7, further comprising:

administering a further modifier of biological response to the patient.

9. The method of therapeutic treatment of claim 8,
wherein said further modifier of biological response is plicamycin.

* * * * *